(12) United States Patent
Gardiner et al.

(10) Patent No.: US 10,894,109 B2
(45) Date of Patent: Jan. 19, 2021

(54) COMPOSITE MATERIALS IN WOUND TREATMENT

(71) Applicant: Mölnlycke Health Care AB, Gothenburg (SE)

(72) Inventors: Eric S. Gardiner, Granville, NY (US); Magnus Paledzki, Brunswick, MA (US)

(73) Assignee: MÖLNLYCKE HEALTH CARE AB, Göteborg (SE)

( * ) Notice: Subject to any disclaimer, the term of this patent is extended or adjusted under 35 U.S.C. 154(b) by 64 days.

(21) Appl. No.: 16/091,782

(22) PCT Filed: Mar. 20, 2017

(86) PCT No.: PCT/EP2017/056475
§ 371 (c)(1),
(2) Date: Oct. 5, 2018

(87) PCT Pub. No.: WO2017/174332
PCT Pub. Date: Oct. 12, 2017

(65) Prior Publication Data
US 2019/0160197 A1 May 30, 2019

(30) Foreign Application Priority Data

Apr. 8, 2016 (EP) ..................................... 16164518

(51) Int. Cl.
*A61L 15/22* (2006.01)
*A61L 15/42* (2006.01)
(Continued)

(52) U.S. Cl.
CPC ............. *A61L 15/225* (2013.01); *A61L 15/28* (2013.01); *A61L 15/425* (2013.01); *A61L 15/60* (2013.01);
(Continued)

(58) Field of Classification Search
None
See application file for complete search history.

(56) References Cited

U.S. PATENT DOCUMENTS

| 4,201,846 A | 5/1980 | Fulmer et al. |
| 2003/0078532 A1* | 4/2003 | Ruszczak .............. A61L 15/225 |
| | | 602/46 |

(Continued)

FOREIGN PATENT DOCUMENTS

| EP | 2498829 A1 | 9/2012 |
| EP | 2659865 A1 | 11/2013 |

(Continued)

OTHER PUBLICATIONS

International Search Report and Written Opinion dated May 18, 2017 by the International Searching Authority for Patent Application No. PCT/EP2017/056475, which was filed on Mar. 20, 2017 and published as WO 2017/174332 on Oct. 12, 2017 (Inventor—Gardiner et al.; Applicant—Mölnlycke Health Case AB) (10 pages).

*Primary Examiner* — Chinessa T. Golden
(74) *Attorney, Agent, or Firm* — Ballard Spahr LLP

(57) ABSTRACT

The present invention relates to a composite material, which is of particular use in wound treatment, and to a method for producing the same composite material. Said composite material comprises a hydrophilic polyurethane foam material comprising a first polyurethane polymer; a hydrophilic fiber material comprising a second polymer, wherein said second polymer is not a polyurethane polymer and wherein said fiber material is capable of absorbing and retaining a fluid. In the composite material according to the present invention, said first polymer is covalently bonded to said second polymer.

18 Claims, 2 Drawing Sheets

(51) Int. Cl.

| | | |
|---|---|---|
| *A61L 15/60* | (2006.01) | |
| *C08L 75/04* | (2006.01) | |
| *C08L 1/26* | (2006.01) | |
| *A61L 15/28* | (2006.01) | |
| *C08G 18/10* | (2006.01) | |
| *C08G 18/73* | (2006.01) | |
| *C08G 18/62* | (2006.01) | |
| *B01J 20/24* | (2006.01) | |
| *B01J 20/26* | (2006.01) | |
| *B01J 20/28* | (2006.01) | |
| *B01J 20/30* | (2006.01) | |
| *B01J 20/32* | (2006.01) | |
| *B29C 39/10* | (2006.01) | |
| *B29K 75/00* | (2006.01) | |
| *B29K 105/04* | (2006.01) | |
| *B29L 31/00* | (2006.01) | |

(52) U.S. Cl.
CPC .......... *B01J 20/24* (2013.01); *B01J 20/267* (2013.01); *B01J 20/28023* (2013.01); *B01J 20/28045* (2013.01); *B01J 20/3085* (2013.01); *B01J 20/3212* (2013.01); *B01J 20/3219* (2013.01); *B01J 20/3274* (2013.01); *B01J 20/3282* (2013.01); *B01J 20/3295* (2013.01); *C08G 18/10* (2013.01); *C08G 18/6212* (2013.01); *C08G 18/73* (2013.01); *C08L 1/26* (2013.01); *C08L 75/04* (2013.01); *A61L 2400/08* (2013.01); *B29C 39/10* (2013.01); *B29K 2075/00* (2013.01); *B29K 2105/04* (2013.01); *B29K 2713/00* (2013.01); *B29K 2995/0092* (2013.01); *B29L 2031/753* (2013.01)

(56) References Cited

U.S. PATENT DOCUMENTS

| | | | | |
|---|---|---|---|---|
| 2004/0153040 | A1* | 8/2004 | Martineau | A61K 9/7023 604/304 |
| 2011/0275972 | A1* | 11/2011 | Rosenberg | A61F 13/00008 602/46 |
| 2013/0197460 | A1* | 8/2013 | Shaw | A61F 13/539 604/368 |

FOREIGN PATENT DOCUMENTS

| | | |
|---|---|---|
| WO | WO-02/45761 A1 | 6/2002 |
| WO | WO-2011/058311 A1 | 5/2011 |
| WO | WO-2013/180832 A1 | 12/2013 |
| WO | WO-2013180832 A1 * 12/2013 | ............. C08L 75/04 |

\* cited by examiner

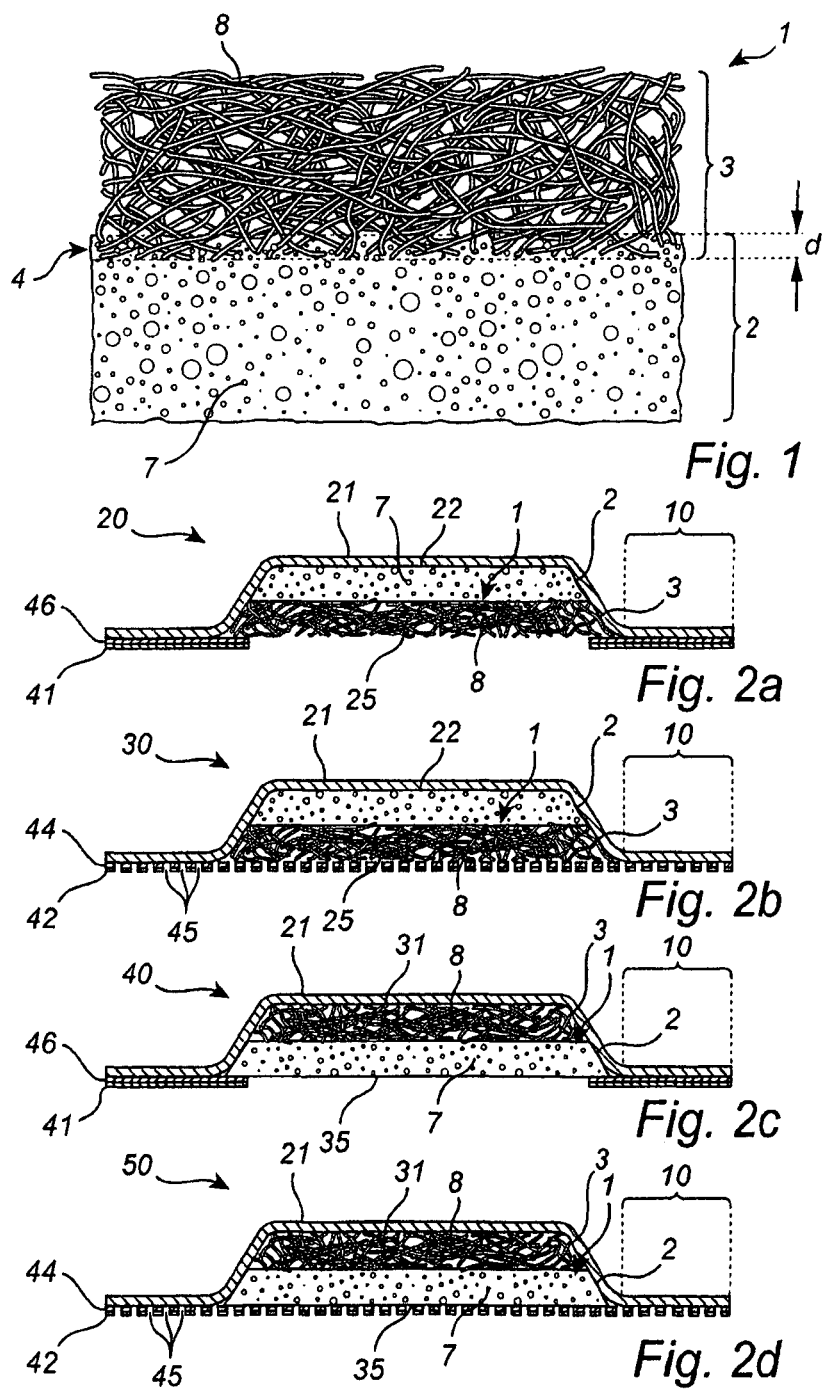

COMPOSITE MATERIALS IN WOUND TREATMENT

CROSS-REFERENCE TO RELATED APPLICATIONS

This application is a U.S. National Phase Application of International Application No. PCT/EP2017/056475, filed Mar. 20, 2017, which claims priority to European Application No. 16164518.9, filed Apr. 8, 2016, each of which are hereby incorporated by reference in their entirety.

FIELD OF THE INVENTION

The present invention relates to a composite material, which is of particular use in wound treatment, and to a method for producing the same composite material.

BACKGROUND OF THE INVENTION

Wound dressings are used to heal and protect wounds. The capability of the wound dressing to absorb and retain exudate from the wound is of paramount importance for the healing process. The liquid handling capacity of a dressing also affects the frequency of dressing changes, which should be minimized to promote wound healing. In particular, hydrophilic materials are used in wound dressing to absorb and retain wound fluids, further particularly hydrophilic foams such as hydrophilic open-cell polyurethane foams. Hydrophilic fibers such as hydrophilic cellulosic fibers, are also known, in principle, to be useful in wound treatment and may also be used in fluid management/liquid handling.

To optimize liquid handling capacity the wound pad in a wound dressing may preferably include a multiple-layer design, wherein each layer preferably is of a different material thus having different capabilities and functionality. To the extent such multiple-layer designs are known from the art, the layers are laminated by means of an adhesive and/or by mechanical lamination. This lamination is associated with several drawbacks. In particular, absorbent materials, for example hydrophilic foams, may swell during use and thus expand when absorbing a liquid, thus stressing the bond between layers and/or increasing thickness, which may result in deformation, e.g. curling or cupping, of dressing and delamination of layers, in particular in the wet state, i.e. while the dressing is in use.

U.S. Pat. No. 7,759,537 discloses a multiple-layer wound dressing including inter alia a wound contacting layer and an absorbent core layer, wherein a "keying layer" of a polyamide web, which is a hot melt adhesive, is provided on the absorbent core layer to bind the absorbent core layer to the wound contact layer. Similarly, EP 2 659 865 relates to a multiple-layer wound dressing comprising inter alia a nonwoven layer sandwiched between two foam layers, wherein all layers can be bonded together using heat activated bonding webs. EP 2 498 829 discloses an absorbent component comprising a wound contacting layer comprising gel forming fibres bound to a foam layer, wherein the foam layer is bound directly to the wound contact layer by an adhesive, polymer based melt layer, by flame lamination or by ultrasound.

However, the use of adhesives or heat bonding webs can impair the liquid transportation of the dressing, and reduce flexibility, absorption and liquid handling capacity of the dressing. Further, mechanical and adhesive bonding of layers requires additional production steps and/or material in the manufacturing process thereof.

Hence, there is a need in the art to provide a wound dressing with different areas, in particular layers, of functionalities that keep their functionality during use, in particular during use as a wound dressing that avoids or minimizes at least one of the disadvantages discussed above.

SUMMARY OF THE INVENTION

In view of the above-mentioned and other drawbacks of the prior art, one object of the present invention is to provide a material having improved durability and point-of-use sustainability, in particular in the treatment of wounds, and a method to produce the same, which material, in particular wound dressing does not suffer from the disadvantages outlined above, or at least minimizes the disadvantages.

According to a first aspect of the invention, these and other objects are achieved through a composite material comprising:

a hydrophilic polyurethane foam material comprising a first polyurethane polymer;
a hydrophilic fiber material comprising a second polymer, wherein said second polymer is not a polyurethane polymer;
wherein said fiber material is capable of absorbing and retaining a fluid,
wherein said hydrophilic polyurethane foam material is, or is comprised in, a foam layer, and said hydrophilic fiber material is, or is comprised in, a fiber layer, wherein the thickness of said foam layer and/or said fiber layer, independently, is at least 100 µm, and
wherein said first polymer is covalently bonded to said second polymer.

In the claims, the terms "comprising" and "comprise(s)" do not exclude other elements or steps, and the indefinite article "a" or "an" does not exclude a plurality of elements or steps. For example, the hydrophilic polyurethane foam material comprising a first hydrophilic polymer may comprise additional polymer(s), in particular another polyurethane polymer and/or another (additional) polymer that is not a polyurethane polymer.

The mere fact that certain measures are recited in mutually different dependent claims does not indicate that a combination of these measured cannot be used to advantage.

The general concept underlying the present invention is based on the realization that a hydrophilic fiber material can be covalently bonded to a hydrophilic polyurethane foam material in situ, using the process of forming said polyurethane foam material. In particular, a hydrophilic fiber material, with reactive groups such as hydroxyl or amine groups, can be covalently bonded to a polyurethane foam material by adding said hydrophilic fiber material to an aqueous pre-polymer composition comprising isocyanate groups, so that the functional groups of the hydrophilic fiber material react with the isocyanate groups thereby forming covalent bonds, at the (progressing) interface of said two materials, whilst at the same time producing the hydrophilic polyurethane foam.

In accordance with the present invention, the term 'hydrophilic' is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups. Preferably, the term 'hydrophilic' refers to the water-permeability property of a material or the water-attracting property of a molecule.

In the context of a material with pores (such as, for example, open-cell foams) or materials with through-holes, such a material is 'hydrophilic' if the material wicks up water. In the context of a material without pores or any through-holes, such a material is considered 'hydrophilic' if it essentially does not resist the flow of water into or through the material. In accordance with the present invention, both the polyurethane foam material and the fiber material are 'hydrophilic' as defined above.

In accordance with the present invention, the term 'composite material' is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a multicomponent material comprising multiple, different (non-gaseous) phase domains, in which at least one type of phase domain is a continuous phase, preferably in which both phase domains are a continuous phase. In accordance with the present invention, the composite material comprises at least one the polyurethane foam material and at least one fiber material.

In accordance with the present invention, the term 'fiber' is to be understood as generally referring to threads or threadlike structures.

The composite material according to the invention exhibits superior bonding properties between the at least two distinct materials (foam and fiber), as compared with known lamination techniques. In particular, the inventors have demonstrated that the composite material, for example when the composite material is realized as a foam layer covalently bonded to a fiber layer, exhibits high peel strength between said layers, even in a wetted state. The inventors have also realized that the formation of covalent bonds between a hydrophilic foam layer and a hydrophilic fiber layer accommodates for the swelling of one or of both hydrophilic layer(s).

In embodiments of the invention, the first polymer is covalently bonded to the second polymer by at least one urethane linkage or urea linkage, wherein the urethane linkage or the urea linkage derives from a reaction between at least one hydroxyl group, or at least one amine group, respectively, of the second polymer of the hydrophilic fiber material and at least one isocyanate group of a prepolymer as used to obtain the first polyurethane polymer of the hydrophilic foam material.

In accordance with the present invention, the term 'covalent bond' is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a region of relatively high electron density between nuclei which arises at least partly from sharing of electrons and gives rise to an attractive force and characteristic internuclear distance.

A "layer" as used in accordance with the present invention should be understood to have a continuous extension in one plane (x and y direction) and a thickness perpendicular to said plane (z direction).

In embodiments of the invention, the hydrophilic foam material is, or is comprised in, a foam layer, and the hydrophilic fiber material is, or is comprised in, a fiber layer, wherein the thickness of said first layer and/or said second layer, independently, is at least 250 µm, preferably at least 1 mm.

In embodiments of the invention, the fiber layer and/or the foam layer comprise(s) a first sublayer and a second sublayer.

In embodiments of the invention, the hydrophilic fiber material may entirely consist of or comprise a non-woven material.

In accordance with the present invention, the term 'non-woven' is to be understood as generally referring to any network of fibers that are held together by interlocking or bonding, in particular by chemical (solvent) or thermal means, and not by means of being woven or knitted.

In embodiments of the invention, the peel strength between the fiber layer and the foam layer in the composite material is at least 200 g/cm, preferably at least 300 g/cm, more preferably at least 400 g/cm or at least 500 g/cm, as measured by standard method ASTM D6862-11 ($11^{th}$ revision).

In embodiments of the invention, a physical penetration depth at the interface between the foam layer and the fiber layer, at which interface said first polyurethane polymer is covalently bonded to said second polymer, is less than 200 µm, preferably less than 100 µm, such as less than 50 µm. In embodiments of the invention, the physical penetration depth at the interface between the foam layer and the fiber layer, at which interface said first polyurethane polymer is covalently bonded to said second polymer, is in the range of 25 to 200 µm, preferably 25 to 100 µm.

The covalent bonding between the first material and the second material can be achieved with minimal physical entanglement of the first and the second material, as compared with prior art lamination techniques, such as adhesive and mechanical bonding, wherein physical interaction in the interaction volume is the actual mechanism of bonding. Minimizing the physical penetration depth is advantageous as the absorption and/or retaining capacity of the materials may be impaired in the physical interaction volume.

The term "physical interaction volume" as used herein means a volume at the interfacial region between the foam and the fiber layers, which volume comprises both the hydrophilic foam material and the hydrophilic fiber material, which materials are covalently bonded by said at least one urethane linkage or urea linkage. The term "physical penetration depth" means the depth of the physical interaction volume in the direction of the thickness of the layers.

In embodiments of the invention, the composite material is characterized by a free swell absorptive capacity, corresponding to the maximum absorptive capacity, of at least 3 times its own weight as measured by EN 13726-1:2002.

In embodiments of the invention, the second polymer of the hydrophilic fiber material is or comprises at least one polymer selected from the group consisting of polyvinyl alcohol (PVA), preferably cross-linked polyvinyl alcohol, polysaccharides such as cellulose and derivatives thereof.

The term "cross-linked" is used herein to describe a material comprising a plurality polymeric molecules which are interlinked by a chemical bond, in particular a covalent bond or an ionic bond, or by a physical cross-link e.g. in thermoplastic elastomers.

In embodiments of the invention, the second polymer of the hydrophilic fiber material is or comprises crosslinked polyvinyl alcohol or carboxymethylcellulose (CMC). In embodiments of the invention, the second polymer of the hydrophilic fiber material is or comprises crosslinked polyvinyl alcohol. In embodiments of the invention, the second polymer of the hydrophilic fiber material is or comprises carboxymethylcellulose.

In embodiments of the invention, the polyvinyl alcohol (PVA) is cross-linked, preferably by heat treatment.

In embodiments of the invention, the hydrophilic fiber material is characterized by a fluid retention capacity of at least 30%, preferably at least 40% or at least 50%, more preferably at least 60% or at least 70%, wherein the fluid retention capacity is defined as the capability of the hydrophilic fiber material to retain Solution A, having first absorbed a maximum amount of Solution A according to EN 13726-1:2002, when exposed to a pressure of 40 mmHg for two minutes. The fluid retention capacity given in percentage (%) corresponds to the amount of residual moisture divided by the maximum absorption as determined according to EN 13726-1:2002.

Solution A, as defined in EN 13726-1, consists of a sodium chloride and calcium chloride solution containing 142 mmol of sodium ions and 2.5 mmol of calcium ions as the chloride salts. This solution has an ionic composition comparable to human serum or wound exudate. Said solution is prepared by dissolving 8.298 g of sodium chloride and 0.368 g of calcium chloride dihydrate in deionized water up to the "1 L" marking in a volumetric flask.

In embodiments of the invention, the first polyurethane polymer of the polyurethane foam material is obtained from a prepolymer comprising or being an isocyanate-capped polyol or isocyanate-capped polyurethane.

In embodiments of the invention, said polyol is selected from the group consisting of polyester polyols, polyacrylate polyols, polyurethane polyols, polycarbonate polyols, polyether polyols, polyesterpolyacrylate polyols, polyurethane polyacrylate polyols, polyurethane polyester polyols, polyurethane polyether polyols, polyurethane polycarbonate polyols and polyester polycarbonate polyols, among others, in particular polycondensates of di or optionally tri-, and tetraols as well as di or optionally tri- and tetracarboxylic acids or hydroxycarboxylic acids or lactones.

Exemplary suitable diols are ethylene glycol, butylene glycol, diethylene glycol, triethylene glycol, polyalkylene glycols such as polyethylene glycol, and also 1,2-propanediol, 1,3-propanediol, 1,3-butanediol, 1,4-butanediol, 1,6-hexanediol and isomers, neopentyl glycol or neopentyl glycol hydroxypivalate, In addition, polyols such as trimethylolpropane, glycerol, erythritol, pentaerythritol, trimethylolbenzene or trishydroxyethyl isocyanurate are also within the scope of the present invention.

In embodiments of the invention, said polyol is a polyethylene glycol (polyethylene oxide). Accordingly, in embodiments of the invention, the prepolymer is or comprises an isocyanate-capped polyethylene glycol.

In embodiments of the invention, the prepolymer derives from a reaction between said polyol and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof.

In embodiments of the invention, the prepolymer derives from a reaction between said polyol and a diisocyanate compound that is aliphatic. In embodiments of the invention, the diisocyanate compound is or comprises hexamethylene diisocyanate (HDI). Accordingly, in embodiments of the invention, the prepolymer is or comprises an hexamethylene isocyanate-capped polyol or hexamethylene isocyanate-capped polyurethane.

In embodiments of the invention, the prepolymer is or comprises a hexamethylene isocyanate-capped polyethylene glycol.

In embodiments of the invention, the content of the diisocyanate compound, in the prepolymer reaction mixture of the diisocyanate compound and the polyol, is at least 15% (w/w) (relative to the total weight of the diisocyanate and the polyol in the prepolymer reaction mixture). In embodiments of the invention, the content of the diisocyanate compound, in the prepolymer reaction mixture of the diisocyanate compound and the polyol, is 15-60%, preferably 20-50% (w/w).

In embodiments of the invention, the hydrophilic polyurethane foam material is an open-cell porous hydrophilic foam having a density of 60 to 180 kg/m$^3$ as measured according to standard method ISO 845:2006.

As used herein, the term "open-cell" refers to the pore structure of the foam, wherein the pores in an open-cell pore structure are connected to each other and form an interconnected network.

According to a second aspect of the invention, the above-mentioned and other objects are achieved by means of providing a wound dressing comprising the composite material according to the invention.

In embodiments of the invention, the wound dressing comprises the hydrophilic foam material as a foam layer and the hydrophilic fiber material as a fiber layer, preferably in the form of a sequence of layers, wherein the wound dressing further comprises at least one further layer, preferably a backing and/or an adhesive layer or coating, preferably two or more of these further layers.

In embodiments of the invention, the wound dressing comprises the hydrophilic foam material as a foam layer and the hydrophilic fiber material as a fiber layer, and wherein the wound dressing further comprises a backing layer overlaying a top side of the fiber layer, said top side being opposite to the side covalently bonded to said foam layer. Thereby, the foam layer may have a side facing the wound and may thus function as a direct or indirect wound contact layer, to absorb and/or retain wound exudate and/or transport wound exudate from the wound to the above fiber layer.

In embodiments of the invention, the wound dressing comprises the hydrophilic foam material as a foam layer and the hydrophilic fiber material as a fiber layer, and wherein the wound dressing further comprises a backing layer overlaying a top side of the foam layer, said top side being opposite to the side covalently bonded to said fiber layer. Thereby, the fiber layer may have a side facing the wound and may thus function as a direct or indirect wound contact layer, to absorb and retain wound exudate and/or transport wound exudate from the wound to the above foam layer.

According to a third aspect of the invention, the above-mentioned and other objects are achieved by means of a method for producing a composite material comprising the steps of:
(i) preparing an aqueous mixture comprising a prepolymer;
(ii) casting said aqueous mixture from step (i) onto a carrier material;
(iii) applying, before said aqueous mixture is essentially completely cured, a layer of a fiber material capable of absorbing and retaining a liquid, on top of said aqueous mixture, as cast onto said carrier material;
(iv) allowing said aqueous mixture to essentially completely cure, thereby producing a composite material comprising a foam layer covalently bonded to said layer of fiber material;
(iv) optionally drying said composite material.

As already outlined above, the term "comprising" does not exclude the presence of other steps or elements. In particular, the aqueous mixture may comprise additional prepolymers and/or other components that are not prepolymers.

In accordance with the present invention, the term 'prepolymer' is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a polymer or oligomer the molecules of which are capable of entering, through reactive groups, into further polymerization and thereby contributing more than one structural unit to at least one type of chain of the final polymer.

In accordance with the present invention, the term 'carrier material' refers to any material, in particular substrate, preferably layer (as defined above), which can accommodate and support the cast-on aqueous mixture.

The term "cure" as used in accordance with the present invention means formation of cross-linking bonds between the polymers of the prepolymer in the aqueous mixture, in particular the cross-linking bond is or comprises urethane bond formed through reaction between an hydroxyl group on a first polymer and an isocyanate (NCO) group on a second polymer, or a urea bond formed through reaction between an amine group on a first polymer and an isocyanate (NCO) group on a second polymer.

In embodiments of the invention, the step (i) of preparing an aqueous mixture comprising a prepolymer includes the step of mixing said prepolymer with water.

In embodiments of the invention, the degree of curing of said aqueous mixture is less than 80%, preferably less than 50%, at the stage of applying said layer of a fiber material in step (iii).

The term "degree of curing" as used herein means the percentage of isocyanate groups that have reacted as measured by Fourier Transform Infrared Spectroscopy (FTIR), i.e. a 100% degree of curing means that essentially all isocyanate (NCO) groups have reacted, whereas 0% degree of curing means that essentially no isocyanate (NCO) groups have reacted. The amount of NCO groups, and thus the corresponding degree of curing, at different stages of the method of producing the composite material can be monitored by FTIR (the number NCO groups corresponding to 0% degree of curing is measured before the prepolymer composition is mixed with water, i.e. before step step (i). The terms "completely cured" and "cure completely" as used in accordance with the present invention mean a degree of curing of 90-100%.

In embodiments of the invention, the water content of said aqueous mixture is less than 40% w/w (relative to the total weight of the aqueous mixture), preferably less than 30% w/w, preferably less than 25% w/w. In embodiments of the invention, the water content of said aqueous mixture is 5 to 40% w/w. In embodiments of the invention, the water content of said aqueous mixture is 5 to 30% w/w. In embodiments of the invention, the water content of said aqueous mixture is from 5 to 25% w/w. In embodiments of the invention, the water content of said aqueous mixture is 5 to 20% w/w. In embodiments of the invention, the water content of said aqueous mixture is 10 to 40% w/w. In embodiments of the invention, the water content of said aqueous mixture is 10 to 30% w/w. In embodiments of the invention, the water content of said aqueous mixture is from 10 to 25% w/w. In embodiments of the invention, the water content of said aqueous mixture is 15 to 20% w/w.

Water absorption by the fiber layer, when applied to the aqueous mixture in step iii), should advantageously be minimized as such water absorption can result in e.g. swelling and/or gelling of the fibers in the fiber layer which in turn can negatively affect the physical integrity and/or the strength of the fibers. In addition, water absorption by the fibers may also result in a larger physical penetration depth and thus increased physical interaction volume, which volume, as discussed above, should preferably be minimized as the absorption and/or retaining capacity of the materials in the physical interaction volume may be impaired. Thus, the water content in the aqueous mixture may advantageously be adapted such that the minimum amount of water required to produce a foam is used. By adapting the water content in the aqueous mixture to be less than 40% w/w, preferably less than 30% w/w, such as below 25% w/w, a substantial amount of the water present in the aqueous mixture can be absorbed and retained by the swelling foam during curing step (iv). Thereby, the amount of water that can be absorbed in the fiber layer in the manufacturing process of the composite material is reduced.

In embodiments of the invention, the prepolymer is or comprises a an isocyanate-capped polyol or isocyanate-capped polyurethane. In embodiments of the invention, the prepolymer derives from a reaction between a polyol, and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof.

In embodiments of the invention, the prepolymer derives from a reaction between a polyol, such a polyethylene glycol, and hexamethylene diisocyanate (HDI). In embodiments of the invention, the prepolymer is or comprises an hexamethylene isocyanate-capped polyol, preferably hexamethylene isocyanate-capped polyethylene glycol, or an hexamethylene isocyanate-capped polyurethane.

In embodiments of the invention, the prepolymer derives from a reaction between a polyol and toluene diisocyanate (TDI). In embodiments of the invention, the prepolymer is or comprises a toluene isocyanate-capped polyol, preferably toluene isocyanate-capped polyethylene glycol, or a toluene isocyanate-capped polyurethane In embodiments of the invention, the prepolymer derives from a reaction between a polyol and methylene diphenyl diisocyanate (MDI). In embodiments of the invention, the prepolymer is or comprises a methylene diphenyl isocyanate-capped polyol, preferably methylene diphenyl isocyanate-capped polyethylene glycol, or a methylene diphenyl isocyanate-capped polyurethane.

BRIEF DESCRIPTION OF THE DRAWINGS

These and other aspects of the invention will now be shown in more detail, with reference to the appended drawings showing an exemplary embodiment of the invention, wherein:

FIG. 1 is a cross-sectional view of an embodiment of a composite material according to the invention; and FIGS. 2a-h are cross-sectional views of embodiments of a wound dressing according to the invention.

DESCRIPTION OF EMBODIMENTS OF THE INVENTION

Figure 2E:
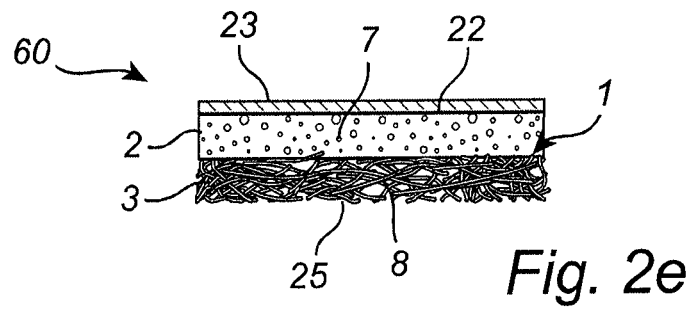

In the following description, detailed embodiments of the present invention are described, with reference to the accompanying drawings, which are exemplary illustrations of embodiments of the invention.

FIG. 1 illustrates an embodiment of a composite material 1 according to the invention. The composite material 1 comprises a hydrophilic foam layer 2 of a hydrophilic polyurethane foam material 7 comprising a first polymer; and a hydrophilic fiber layer 3 of a hydrophilic fiber material 8 comprising a second polymer capable of absorbing and retaining a fluid, wherein the second polymer is not a polyurethane polymer, and wherein the first polymer is covalently bonded to the second polymer by at least one urethane linkage or urea linkage. The at least one urethane linkage or urea linkage is formed in the physical interaction volume 4 at the interface between the hydrophilic foam layer 2 and the hydrophilic fiber layer 3. In embodiments of the invention, the physical interaction depth d, which corresponds to the depth of the physical interaction volume 4 at the interface between the foam 2 and fiber 3 layers, is less than 200 µm, preferably less than 100 µm, more preferably less than 50 µm. For example, in embodiments of the invention the physical interaction depth d is in the range of 10 to 200 µm, such as 50 to 200 µm or 50 to 150 µm, or 50 to 100 µm. In embodiments of the invention the physical interaction depth d is in the range of 10 to 100 µm, such as 10 to 60 µm. The covalent bonding of the foam 2 and fiber 3 layers provides for a minimum physical interaction depth d, as compared with adhesive and mechanical bonding, which is advantageous as the absorption and/or retaining capacity of the materials may be impaired in the physical interaction volume 4.

In embodiments of the invention, the peel strength between the fiber layer 3 and the foam layer 2 in the composite material 1 is at least 200 g/cm, preferably at least 300 g/cm, and more preferably at least 400 g/cm or at least 500 g/cm, as measured according to standard method ASTM D6862-11.

The covalent bonds, provided by the at least one urethane linkage or urea linkage, between the hydrophilic foam layer 2 and the hydrophilic fiber layer 3 provides a composite material 1 with high peel strength as compared laminates bonded with adhesive and/or mechanical bonds. Having a high peel strength is advantageous as delamination of layers 2,3 in the composite material 1 can be avoided or at least minimized, when wetted in particular when composite material 1 is used in a wound dressing.

In embodiments of the invention, the composite material 1 is characterized by a free swell absorptive capacity, corresponding to the maximum absorptive capacity, of at least 3 times its own weight as measured by EN 13726-1:2002, preferably at least 5 times its own weight as measured by EN 13726-1:2002 and more preferably at least 8 times or at least 10 times as measured by EN 13726-1:2002.

In embodiments of the invention, the hydrophilic polyurethane foam layer 2 has a thickness of from 1 mm to 20 mm. In embodiments of the invention, the hydrophilic foam layer 2 has a thickness of from 1 mm to 15 mm. In embodiments of the invention, the hydrophilic foam layer 2 has a thickness of from 1 mm to 10 mm. In embodiments of the invention, the hydrophilic foam layer 2 has a thickness of from 1 mm to 8 mm. In embodiments of the invention, the hydrophilic foam layer 2 has a thickness of from 1 mm to 5 mm.

In embodiments of the invention, the foam material is an open-cell porous hydrophilic foam having a density of 60 to 180 kg/m$^3$, preferably 100 to 150 kg/m$^3$, as measured according to standard method ISO 845:2006.

In embodiments of the invention, the first polyurethane polymer of the hydrophilic polyurethane foam material 7 is obtained from a prepolymer comprising or being an isocyanate-capped polyol or isocyanate-capped polyurethane.

In embodiments of the invention, said polyol is selected from the group consisting of polyester polyols, polyacrylate polyols, polyurethane polyols, polycarbonate polyols, polyether polyols, polyesterpolyacrylate polyols, polyurethane polyacrylate polyols, polyurethane polyester polyols, polyurethane polyether polyoles, polyurethane polycarbonate polyols and polyester polycarbonate polyols, among others, in particular polycondensates of di or optionally tri-, and tetraols as well as di or optionally tri- and tetracarboxylic acids or hydroxycarboxylic acids or lactones. Exemplary suitable diols are ethylene glycol, butylene glycol, diethylene glycol, triethylene glycol, polyalkylene glycols such as polyethylene glycol, and also 1,2-propanediol, 1,3-propanediol, 1,3-butanediol, 1,4-butanediol, 1,6-hexanediol and isomers, neopentyl glycol or neopentyl glycol hydroxypivalate, In addition, polyols such as trimethylolpropane, glycerol, erythritol, pentaerythritol, trimethylolbenzene or trishydroxyethyl isocyanurate are also within the scope of the present invention. In embodiments of the invention, said polyol is a mixture of polyethylene glycol and glycerol. In embodiments of the invention, said polyol is polyethylene glycol (polyethylene oxide).

In embodiments of the invention, the prepolymer derives from a reaction between a polyol and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof.

In embodiments of the invention, the prepolymer derives from a reaction between a polyol and a diisocyanate compound that is aliphatic. In embodiments of the invention, the prepolymer derives from a reaction between a polyol and a diisocyanate compound that is or comprises hexamethylene diisocyanate (HDI).

In embodiments of the invention, the prepolymer derives from a reaction between a polyol and a diisocyanate compound that is aromatic. In embodiments of the invention, the prepolymer derives from a reaction between a polyol and a diisocyanate compound that is or comprises toluene diisocyanate (TDI) or methylene diphenyl diisocyanate (MDI).

In embodiments of the invention, the content of the diisocyanate compound, in the prepolymer reaction mixture of the diisocyanate compound and the polyol, is 15-60% (w/w) (relative to the total weight of the diisocyanate compound and the polyol), preferably 20-50% (w/w).

In embodiments of the invention, the first polyurethane polymer of the hydrophilic polyurethane foam material 7 is obtained from a prepolymer obtained by reacting hexamethylene diisocyanate (HDI) with one or more polyols, such as a polyethylene glycol and/or a glycerol. In embodiment of the invention the prepolymer is, or comprises hexamethylene isocyanate-capped polyethylene glycol.

In embodiments of the invention, the hydrophilic polyurethane foam material 7 is characterized by a free swell absorptive capacity, corresponding to the maximum absorptive capacity, of at least 3 times its own weight as measured by EN 13726-1:2002, preferably at least 5 times its own weight as measured by EN 13726-1:2002 and more preferably at least 8 times or at least 10 times as measured by EN 13726-1:2002.

In embodiments of the invention, the hydrophilic fiber layer 3 has a basis weight of from 10 to 600 g/m$^2$. In embodiments of the invention, the hydrophilic fiber layer 3 has a basis weight of from 50 to 400 g/m$^2$.

In embodiments of the invention, the second polymer of the hydrophilic fiber material 8 may comprise gelling fibers capable of absorbing and retaining a liquid by the formation of a hydrogel. The term "hydrogel" as used in accordance with the present invention, should be understood as relating to a non-fluid polymer network in particular a network formed by crosslinking polymer or by nonlinear polymerization, which network is expanded throughout its whole volume by a fluid.

In embodiments of the invention, the second polymer of the hydrophilic fiber material 8 is or comprises at least one polymer selected from the group consisting of polyvinyl alcohol, preferably crosslinked polyvinyl alcohol (PVA), polysaccharides such as cellulose and derivatives thereof. For example, the second polymer may be a cellulose polymer selected from the group consisting of carboxymethylcellulose, carboxyethylcellulose, hydroxymethylcellulose, hydroxyethylcellulose, hydroxypropylcellulose, hydroxypropylmethylcellulose; chitosan or deacetylated chitin, and algal polysaccharides.

In embodiments of the invention, the second polymer of the hydrophilic fiber material 8 is or comprises crosslinked polyvinyl alcohol or carboxymethylcellulose. In embodiments of the invention, the second polymer of the hydrophilic fiber material 8 is or comprises crosslinked polyvinyl alcohol. In embodiments of the invention, the second polymer of the hydrophilic fiber material 8 is or comprises carboxymethylcellulose.

In embodiments of the invention, the hydrophilic fiber material 8 is characterized by a fluid retention capacity of at least 30%, preferably at least 40% or at least 50%, more preferably at least 60% or at least 70%, wherein the fluid retention capacity is defined as the capability of the fiber material to retain Solution A, having first absorbed a maximum amount of Solution A according to EN 13726-1:2002, when exposed to a pressure of 40 mmHg for two minutes. The fluid retention capacity given in percentage (%) corresponds to the amount of residual moisture divided by the maximum absorption as determined according to EN 13726-1:2002. In embodiments of the invention, the hydrophilic fiber material 8 is characterized by a fluid retention capacity of at least 80% or at least 90%. A high retention capacity is inter alia useful if the composite material is used as or in a wound dressing, in particular, if the composite material is in direct contact with the wound, a high retention capacity of the hydrophilic fiber material lowers the risk of leakage and e.g. skin maceration as more liquid is contained within the composite material even when subjected to a pressure.

In embodiments of the invention, the hydrophilic fiber material 8 is characterized by a free swell absorptive capacity, corresponding to the maximum absorptive capacity, of at least 3 times its own weight as measured by EN 13726-1:2002, preferably at least 5 times its own weight as measured by EN 13726-1:2002 and more preferably at least 8 times or at least 10 times as measured by EN 13726-1:2002.

FIGS. 2a-h illustrate exemplary embodiments of wound dressings 20, 30, 40, 50, 60, 70, 80, 90 comprising the composite material 1, as realized in the form of a sequence of layers, according to the invention. The wound dressings 20, 30, 40, 50, 60, 70, 80, 90 shown in FIGS. 2a-h thus comprise the hydrophilic polyurethane foam material 7 as a foam layer 2 and the hydrophilic fiber material 8 as a fiber layer 3.

In embodiments of the invention, as illustrated in FIGS. 2a-b and FIGS. 2e-f, the wound dressings 20, 30, 60, 70 further comprise a backing layer 21, 23 overlaying a top side 22 of the foam layer 2, wherein the top side 22 is opposite to the side covalently bonded to the fiber layer 3. Thereby, the fiber layer 3 has a wound facing side 25 which can function as a direct or indirect wound contact layer, to absorb and retain wound exudate and/or transport wound exudate from the wound to the above foam layer 2. In this configuration, wherein the foam layer 2 is facing away from the wound, the foam layer 2 can also function to accommodate for, and thus protect the wound from, external physical pressure on the wound dressing.

In embodiments of the invention, as shown in FIGS. 2c-d and FIGS. 2g-h, the wound dressings 40, 50, 80, 90 further comprise a backing layer 21, 23 overlaying a top side 31 of the fiber layer 3, wherein the top side 31 being opposite to the side covalently bonded to the foam layer 2. Thereby, the foam layer 2 has a wound facing side 35 which can function as a direct or indirect wound contact layer, to absorb and retain wound exudate and/or transport wound exudate from the wound to the above fiber layer 3. In this configuration, wherein the foam layer 2 is facing the wound, the foam layer 2 can be adapted to provide rapid absorption of wound exudate.

In embodiments of the invention, as shown in FIGS. 2a-d, the backing layer 21 extends outside the peripheral portion of the layers of the composite material, to define a border portion 10 of the backing layer thus surrounding the peripheral portion of the layers of the composite material, thereby providing a so-called island dressing.

In embodiments of the invention, the backing layer 21, 23 is preferably vapor permeable. The backing layer 21, 23 may be a plastic film, for example, comprising or consisting of polyurethane, polyethylene, or polypropylene. In embodiments of the invention, the backing layer 21, 23 is a polyurethane film having a thickness in the range of 10-100 μm, for example, 10-80 μm such as 10-50 μm.

As schematically illustrated in FIGS. 2a-d, FIGS. 2f-h, the wound dressings 20, 30, 40, 50, 70, 80, 90 include an adhesive layer or coating 41, 42, 43 to adhere the wound dressing to a wound and/or the surrounding skin surface. In embodiments of the invention, the adhesive layer or coating may be a silicone based adhesive or an acrylic based adhesive, preferably the adhesive layer or coating is a silicone based adhesive. The term "coating" should, in accordance with the present invention, be understood as at least one continuous layer on a surface, or a discontinuous cover on a surface e.g. plurality of particles distributed on an area of a surface.

As shown in FIG. 2b, FIG. 2d, FIG. 2f and FIG. 2h, the wound dressings 30, 50, 70, 90 include a perforated layer 44, for example made of a polyurethane film, wherein an adhesive coating 42 is provided on the non-perforated portions of the perforated layer 44. The perforated layer 44 includes a plurality of openings 45 (or through holes) of any desirable size and shape. The shape and size of the openings 45 may be adapted to achieve a desirable liquid transport from the wound to the above layers of the composite material 1.

In embodiments of the invention, as illustrated in FIG. 2b and FIG. 2d, the perforated layer 44 with the adhesive coating 42 may be provided on the wound facing surface 25, 35 of the foam layer 2 or fiber layer 3, respectively, wherein the perforated layer 44 extends outside the peripheral portion of the layers of the composite material 1 and is attached to the border portion 10 of the backing layer 21.

Figure 2F:
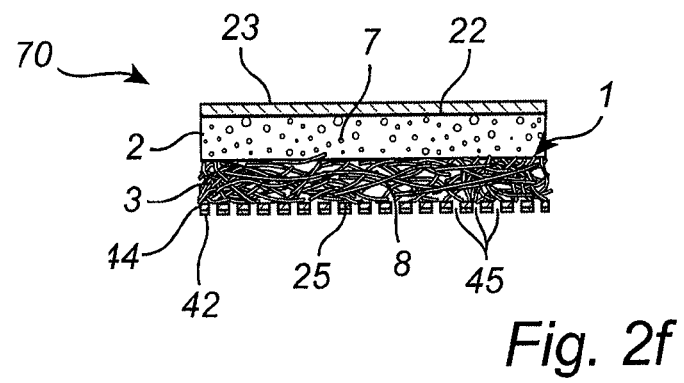
Figure 2G:
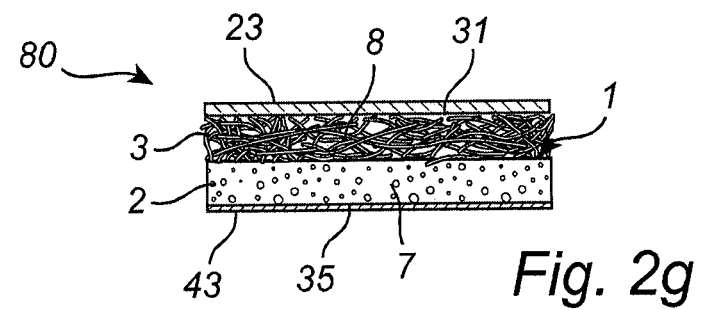
Figure 2H:
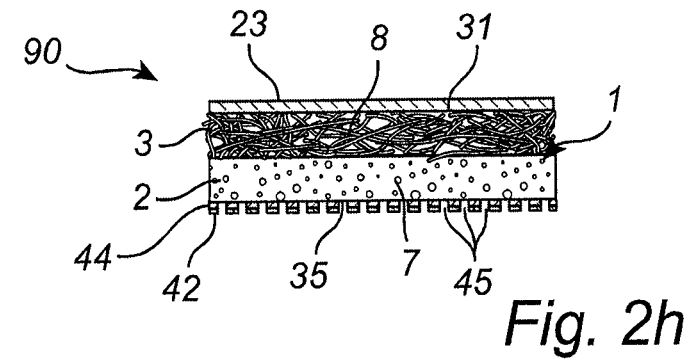

In alternative embodiments, as shown in FIG. 2f and FIG. 2h, the footprint of the perforated layer 44 corresponds to the footprint of the composite material 1. In embodiments of the invention, as shown in FIG. 2g the adhesive coating 43 is provided directly on the wound facing surface 35 of the foam layer 2. In embodiments of the invention, as shown in FIG. 2a and FIG. 2c, an adhesive coating 41 is provided on a continuous plastic film 46, for example a polyurethane film as discussed above, which continuous plastic film 46 is arranged adjacent to a peripheral portion of the layers of the composite material 1, wherein the continuous film 46 extends away from said peripheral portion and is attached to the border portion 10 of the backing layer 21. In further embodiments (not shown) and adhesive coating may be provided directly on a skin facing surface of the border portion 10 of the backing layer 21.

In embodiments of the invention, the fiber layer 3 and/or the foam layer 2 comprise(s) a first sublayer and a second sublayer (not shown). For example, the fiber layer 3 may include a first sublayer of a non-woven absorbent layer and a second sublayer comprising absorbent fibers or particles. For example, the first sublayer may be a non-woven layer covalently bonded to the foam layer 2 and the second sublayer may comprise a mixture of superabsorbent fibers and/or superabsorbent particles and/or non-absorbent fibers, which mixture may be airlaid, e.g. by spraying, needling, or carding, on a side of the first sublayer opposite to the side bonded to the foam layer.

The terms "superabsorbent fibers" or "superabsorbent particles" as used in accordance with the present invention are generally understood to be water-swellable, water-insoluble organic or inorganic materials capable of absorbing at least about 20 times their own weight as measured by EN 13726-1:2002. Organic materials suitable for use as a superabsorbent material preferably include natural materials such as polysaccharides (including modified polysaccharides such as carboxymethyl cellulose (CMC)), polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyvinyl pyridines.

In embodiments of the invention, the hydrophilic polyurethane foam material 7 and/or the hydrophilic fiber material 8 comprises an antimicrobial agent. In embodiments of the invention, the antimicrobial agent comprises silver. In embodiments of the invention, the silver is metallic silver. In embodiments of the invention, the silver is a silver salt. In embodiments of the invention, the silver salt is silver sulfate, silver chloride, silver nitrate, silver sulfadiazine, silver carbonate, silver phosphate, silver lactate, silver bromide, silver acetate, silver citrate, silver CMC, silver oxide. In embodiments of the invention, the silver salt is silver sulfate. In embodiments of the invention, the antimicrobial agent comprises a monoguanide or biguanide. In embodiments of the invention, the monoguanide or biguanide is chlorhexidine digluconate, chlorhexidine diacetate, chlorhexidine dihydrochloride, polyhexamethylenebiguanide (PHMB) or a salt thereof, or polyhexamethylenemonoguanide (PHMG) or a salt thereof. In embodiments of the invention, the biguanide is PHMB or a salt thereof. In embodiments of the invention, the antimicrobial agent comprises a quaternary ammonium compound. In embodiments of the invention, the quaternary ammonium compound is cetylpyridinium chloride, benzethonium chloride, or poly-DADMAC. In embodiments of the invention, the antimicrobial agent comprises triclosan, sodium hypochlorite, copper, hydrogen peroxide, xylitol, or honey.

The composite material according to the invention is produced through a method comprising the steps of: (i) preparing an aqueous mixture comprising a prepolymer; (ii) casting the aqueous mixture from step (i) onto a carrier material; (iii) applying, before said aqueous mixture is essentially completely cured, a layer of a fiber material capable of absorbing and retaining a liquid, on top of said aqueous mixture as cast onto the carrier material; (iv) allowing said aqueous mixture to essentially completely cure, thereby producing a composite material comprising a foam layer covalently bonded to said layer of fiber material; and (v) optionally drying said composite material.

In embodiments of the invention, the degree of curing of the aqueous mixture is less than 80%, preferably less than 50%, at the stage of applying the layer of a fiber material in step (iii). The steps (i)-(iii) are advantageously performed in immediate sequential steps to ensure a low degree of curing in the aqueous mixture when the fiber layer is applied, thereby ensuring enough reactivity in aqueous mixture to achieve sufficient amount of covalent bonds (urethane or urea linkages) between the foam and fiber material.

In embodiments of the invention, the water content of the aqueous mixture is less than 40% w/w (relative to the total weight of the aqueous mixture), preferably less than 30% w/w, preferably less than 25% w/w. In embodiments of the invention, the water content of said aqueous mixture is 10 to 40% w/w. In embodiments of the invention, the water content of said aqueous mixture is 10 to 30% w/w. In embodiments of the invention, the water content of said aqueous mixture is 10 to 25% w/w. In embodiments of the invention, the water content of said aqueous mixture is 15 to 20% w/w. In embodiments of the invention, the water content of said aqueous mixture is 5 to 30% w/w. In embodiments of the invention, the water content of said aqueous mixture is 5 to 25% w/w. In embodiments of the invention, the water content of said aqueous mixture is 5 to 20% w/w.

The water content in the aqueous mixture may advantageously be adapted such that the minimum amount of water required to produce a foam is used. Minimizing the use of water in the aqueous mixture is advantageous inter alia in the drying step (v) of the method as low amount of water in the composite material means a low shrinkage of the layers in the composite during the drying step, which thus reduce the stress on the covalent bonds between the layers. Minimizing the amount of water in the aqueous mixture provides for an aqueous mixture with a higher viscosity which is advantageous in order to minimize penetration of the aqueous mixture into the foam layer.

In embodiments of the invention, the step (i) of preparing an aqueous mixture comprising a prepolymer includes the step of mixing said prepolymer composition comprising said prepolymer with water.

In embodiments of the invention, the prepolymer is or comprises an isocyanate-capped polyol or isocyanate-capped polyurethane. In embodiments of the invention, the prepolymer derives from a reaction between a polyol, and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof. In embodiments of the invention, the diisocyante compound is hexamethylene diisocyanate (HDI). In embodiments of the invention, the diisocyante compound is toluene diisocyanate (TDI). In embodiments of the invention, the diisocyante compound is methylene diphenyl diisocyanate (MDI). In embodiments of the invention, the polyol is polyethylene glycol.

In embodiments of the invention, the aqueous mixture further comprises at least one surfactant, preferably a non-ionic surfactant.

The advantages of the invention have been demonstrated in the following Examples.

EXAMPLES

Methods of Preparing Composite Materials

Composite materials according to embodiments of the invention were prepared, at standard laboratory conditions (at room temperature unless otherwise stated).

Example 1

A first composite material was prepared by the following steps (1-6): (1) an aqueous mixture consisting of the following chemicals were prepared (commercially available from BASF): sodium bicarbonate 1.5% w/w, Pluronic® L62 0.01% w/w, and citric acid 0.002% w/w; (2) the aqueous mixture was mixed with Baymedix FP-505 (an HDI based prepolymer composition commercially available from Covestro) at a 1:5 ratio by weight (i.e. 1 part of aqueous mixture to 5 parts of HDI based prepolymer) to give an emulsion mixture; (3) the emulsion mixture was poured onto and spread out on a casting paper (20×30 cm); (4) an Exufiber® dressing (20×30 cm; 260 gsm, including cross-linked PVA fibers, commercially available from Mölnlycke Health Care) was applied on top of the emulsion; (5) the product was allowed to cure at standard condition (at room temperature) to give a foam thickness of about 3 mm (foam thickness is controlled by adapting the thickness of spread of the emulsion mixture in step (3); and (6) the resulting composite product was dried in an oven at 40° C. for 10 minutes per side. Steps 1 to 4 were done in immediate sequential steps, wherein steps 2-4 should preferably be completed within less than 4 minutes to thereby ensure a low degree of curing (sufficient reactivity left) in the emulsion mixture when step 4 is initiated. A test piece (prototype A) was prepared by die-cutting the dried composite product to a size of approximately 10×10 cm.

Example 2

A second composite material was prepared on an automated Pilot Production Line by the following steps (1-6): (1) an aqueous mixture was prepared using Pluronic® L-62 (commercially available from BASF) at a concentration of 0.14 wt %; (2) the aqueous mixture was then metered and mixed with Trepol® B-1 (a TDI based prepolymer commercially available from Rynel Inc.) at a ratio of 1:3.2 by weight (i.e. 1 part of aqueous mixture to 3.2 parts of TDI based prepolymer), using a standard Pin-type mixer to give an emulsion mixture; (3) when thoroughly mixed the emulsion (produced in step 2) was fed through a coat-hanger die and cast onto a siliconized casting paper; (4) an Exufiber® dressing material was fed from a roll and applied to the top of the curing emulsion; (5) the product was allowed to cure at standard condition (at room temperature) to give a foam thickness of about 2.5 mm (foam thickness is controlled by adapting the thickness of spread of the emulsion mixture in step 3); and (6) the resulting composite product was conveyed while drying (at 40° C. for 20 minutes) to a wind-up roller. Steps 1 to 4 were done in immediate sequential steps, wherein steps 2-4 should preferably be completed within less than 2 minutes to thereby ensure a low degree of curing (sufficient reactivity left) in the emulsion mixture when step 4 is initiated.

Example 3

The method of Example 1 was also used to prepare a third composite material wherein an Aquacel® dressing (including CMC fibers; commercially available from ConvaTec) was applied in step 4 (instead of the Exufiber® dressing above).

Method and Result of Measuring Penetration Depth

The penetration depth was measured using a stereoscopic microscope with micrometer scale, that is, the physical interaction volume between the foam and fiber layers was identified using the microscope and the penetration depth, corresponding to the depth of the physical interaction volume in the direction of the thickness of the layers/composite material, was measured using the micrometer scale. The penetration of Prototype A, as measured accordingly, was estimated to be about 50 μm.

Method and Result of Measuring Peel Strength

The peel strength was measured using the standard method ASTM D6862-11 ($11^{th}$ revision, 90 degree peel strength test). The peel strength test on the wound pad of Aquacel® Foam, which pad includes a wound contact layer of non-woven absorbent fibers mechanically bonded to a foam layer, resulted in delamination of the two layers at a force of about 60-100 g/cm (the range indicating different bond strengths across the laminated surfaces of the layers). In contrast, the peel strength test on the Prototype A resulted in material failure (material break) in the foam layer (i.e. not at the interface between foam and fiber layers) at a force of about 500 g/cm. It can thus be concluded that the peel strength between the fiber and foam layer in the composite material of Prototype A is more than 500 g/cm. Thereby, demonstrating the superior bond strength between the layers of the composite material provided by the covalent bonding as compared with the bond strength between the mechanically bonded layers of the wound pad of Aquacel® Foam.

Comparative Material Stability Study Upon Absorption

Prototype A, as prepared above, and the wound pad of Aquacel® Foam which pad includes a wound contact layer of non-woven absorbent fibers mechanically bonded to a foam layer, were test for free swell absorptive capacity, corresponding to the maximum absorptive capacity, as measured by EN 13726-1:2002, however with the following deviations: water was used instead of Solution A of EN 13726-1:2002 and the samples were drained for 5 minutes instead of the 30 seconds as specified in EN 13726-1:2002. The absorption measured accordingly was 11.6 g/g for Prototype A and 15.8 g/g for the wound pad of Aquacel® Foam. Upon adding the wound pad of Aquacel® Foam to water as part of the absorbency testing, the wound pad delaminated within one minute. The wound pad also did not swell to the extent that the foam component of the dressing did, further aiding in the detachment of the two components. Thus, the absorption value for the wound pad of Aquacel® Foam, as given above, is the total of the two delaminated components after draining. In contrast, Prototype A exhibited high material stability and maintained its composite structure during the absorption test, thus clearly demonstrating the strong bonding achieved through the covalent bonds.

Accordingly, the peel strength of the Prototype A is so high that material failure that typically occurs at the interface between laminated layers in known multi-layer structures, in particular when the overall multi-layer structure is wet, in particular when liquid is retained within the multi-layer structure, is not observed for the Prototype A.

Determination of Fluid Retention Capacity

In accordance with the invention "fluid retention capacity" is determined by first measuring the maximum absorption according to EN 13726-1:2002. A rigid template, approximately the same size as the sample with a mass equivalent to 40 mmHg (543.6 g/100 $cm^2$), is subsequently applied to sample (now being soaked with Solution A according to EN 13726-1:2002). After 2 minutes the rigid template is removed and the sample weight is again measured and amount of residual moisture is calculated. The fluid retention capacity (given in %) is calculated by dividing the amount of residual moisture by the maximum absorption as determined according to EN 13726-1:2002. The retention value of an Exufiber® dressing (260 gsm, including cross-linked PVA fibers, commercially available from Mölnlycke Health Care) was determined accordingly to be about 95%.

Solution A, as defined in EN 13726-1, consists of a sodium chloride and calcium chloride solution containing 142 mmol of sodium ions and 2.5 mmol of calcium ions as the chloride salts. This solution has an ionic composition comparable to human serum or wound exudate. Said solution is prepared by dissolving 8.298 g of sodium chloride and 0.368 g of calcium chloride dihydrate in deionized water up to the "1 L" marking in a volumetric flask.

The invention claimed is:

1. A composite material comprising:
   a hydrophilic polyurethane foam material comprising a first polyurethane polymer;
   a hydrophilic fiber material comprising a second polymer, wherein said second polymer is not a polyurethane polymer;
   wherein said fiber material is capable of absorbing and retaining a fluid,
   wherein said hydrophilic polyurethane foam material is comprised in a foam layer, and said hydrophilic fiber material is comprised in a fiber layer, wherein the thickness of said foam layer and/or said fiber layer, independently, is at least 100 µm, and
   wherein said first polyurethane polymer is covalently bonded to said second polymer.

2. The composite material according to claim 1, wherein said first polymer is covalently bonded to said second polymer by at least one urethane linkage or at least one urea linkage, wherein said urethane linkage or said urea linkage is derived from a reaction between at least one hydroxyl group or at least one amine group, respectively, of said second polymer of said hydrophilic fiber material and at least one isocyanate group of a prepolymer as used to obtain said first polyurethane polymer of said hydrophilic polyurethane foam material.

3. The composite material according to claim 1, wherein said hydrophilic fiber material comprises a non-woven material.

4. The composite material according to claim 1, wherein the thickness of said foam layer and/or said fiber layer, independently, is at least 250 µm, respectively.

5. The composite material according to claim 4, wherein said fiber layer and/or said foam layer comprises a first sublayer and a second sublayer.

6. The composite material according to claim 1, wherein the second polymer of said hydrophilic fiber material comprises at least one polymer selected from the group consisting of polyvinyl alcohol and polysaccharides.

7. The composite material according to claim 1, wherein said first polyurethane polymer of said hydrophilic polyurethane foam material is obtained from a prepolymer comprising an isocyanate-capped polyol or isocyanate-capped polyurethane.

8. The composite material according to claim 7, wherein said first polyurethane polymer of said hydrophilic polyurethane foam material is obtained from a prepolymer comprising isocyanate-capped polyol, wherein the polyol in the said isocyanate-capped polyol is selected from the group consisting of polyester polyols, polyacrylate polyols, polyurethane polyols, polycarbonate polyols, polyether polyols, polyesterpolyacrylate polyols, polyurethane polyacrylate polyols, polyurethane polyester polyols, polyurethane polyether polyols, polyurethane polycarbonate polyols, and polyester polycarbonate polyols.

9. The composite material according to claim 7, wherein said prepolymer is derived from a reaction between a polyol, and a diisocyanate compound selected from the group consisting of hexamethylene diisocyanate (HDI), toluene diisocyanate (TDI), methylene diphenyl diisocyanate (MDI), and isophorone diisocyanate (IPDI), or any mixture thereof.

10. The composite material according to claim 7, wherein said prepolymer is derived from a reaction between a polyol, and a diisocyanate compound that is aliphatic.

11. The composite material according to claim 7, wherein the content of said diisocyanate compound in the prepolymer reaction mixture of said diisocyanate compound and said polyol is at least 15% w/w relative to the total weight of said diisocyanate compound and said polyol in said prepolymer reaction mixture.

12. The composite material according to claim 1, wherein the composite material comprises a physical penetration depth of 25 µm to 200 µm at an interface where the foam layer and the fiber layer overlap, wherein the first polyurethane polymer is covalently bonded to the second polymer in the physical penetration depth.

13. A wound dressing comprising a composite material according to claim 1.

14. The wound dressing according to claim 13, wherein said wound dressing comprises said hydrophilic foam material as a foam layer and said hydrophilic fiber material as a fiber layer, wherein said wound dressing further comprises at least one further layer.

15. A method for producing the composite material according to claim 1, comprising the steps of:
   (i) preparing an aqueous mixture comprising a prepolymer;
   (ii) casting said aqueous mixture from step (i) onto a carrier material;
   (iii) applying, before said aqueous mixture is essentially completely cured, a layer of a fiber material capable of absorbing and retaining a liquid, on top of said aqueous mixture as cast onto said carrier material;
   (iv) allowing said aqueous mixture to essentially completely cure, thereby producing a composite material comprising a foam layer covalently bonded to said layer of fiber material;
   (v) optionally drying said composite material.

16. The method according to claim 15, wherein the water content of said aqueous mixture is less than 40% w/w relative to the total weight of said aqueous mixture.

17. The method according to claim 16, wherein the degree of curing of said aqueous mixture is less than 80% at the stage of applying said layer of a fiber material in step (iii).

18. The method according to claim 15, wherein said prepolymer comprises an isocyanate-capped polyol or isocyanate-capped polyurethane.

* * * * *